United States Patent [19]
Graham

[11] Patent Number: 5,976,125
[45] Date of Patent: Nov. 2, 1999

[54] EXTERNAL DISTRACTOR/FIXATOR FOR THE MANAGEMENT OF FRACTURES AND DISLOCATIONS OF INTERPHALANGEAL JOINTS

[75] Inventor: Thomas J. Graham, Chagrin Falls, Ohio

[73] Assignee: The Cleveland Clinic Foundation, Cleveland, Ohio

[21] Appl. No.: 08/704,957

[22] Filed: Aug. 29, 1996

Related U.S. Application Data

[60] Provisional application No. 60/002,913, Aug. 29, 1995.

[51] Int. Cl.⁶ ................................................... A61B 17/38
[52] U.S. Cl. ............................................................ 606/32
[58] Field of Search ................................ 606/57, 58, 55, 606/56, 59, 54, 72, 73, 90

[56] References Cited

U.S. PATENT DOCUMENTS

| | | |
|---|---|---|
| Re. 31,809 | 1/1985 | Danieletto et al. . |
| 4,096,857 | 6/1978 | Cramer et al. . |
| 4,127,119 | 11/1978 | Kronner . |
| 4,135,505 | 1/1979 | Day . |
| 4,185,624 | 1/1980 | Gentile . |
| 4,187,841 | 2/1980 | Knutson . |
| 4,244,360 | 1/1981 | Dohogne . |
| 4,271,832 | 6/1981 | Evans et al. . |
| 4,308,863 | 1/1982 | Fischer . |
| 4,312,336 | 1/1982 | Danieletto et al. . |
| 4,360,012 | 11/1982 | McHarrie et al. . |
| 4,450,834 | 5/1984 | Fischer . |
| 4,456,004 | 6/1984 | Kenny . |
| 4,475,546 | 10/1984 | Patton . |
| 4,483,334 | 11/1984 | Murray . |
| 4,502,473 | 3/1985 | Harris et al. . |
| 4,535,763 | 8/1985 | Jaquet . |
| 4,541,422 | 9/1985 | de Zbikowski . |
| 4,548,199 | 10/1985 | Agee . |
| 4,554,915 | 11/1985 | Brumfield . |
| 4,564,007 | 1/1986 | Coombs et al. . |
| 4,570,625 | 2/1986 | Harris et al. . |
| 4,573,459 | 3/1986 | Litton . |
| 4,604,997 | 8/1986 | De Bastiani et al. . |

(List continued on next page.)

OTHER PUBLICATIONS

The Dynamic Traction Method; From the Section of Hand Surgery, Departments of Plastic and Orthopaedic Surgery, Rush–Presbyterian–St. Luke's Medical Center and Hand Surgery, Ltd., Chicago, Illinois, vol. 10, No. 2, May 1994.

Mechanical Requirements For Application and Modification of the Dynamic Force Couple Method; Robert T. Buchanan, MD, From the Section of Plastic Surgery, Department of Surgery, University of Oklahoma Health Sciences Center, and Hand & Arm Care Center, Oklahoma City, Oklahoma, vol. 10, No. 2, May 1994.

Unstable Fracture Disclosations of the Proximal Interphalangel Joint of the Fingers: A Preliminary Report of a New Treatment Technique; John M. Agee, MD, Sacramento, California, The Journal of Hand Surgery 1978.

Dynamic Digital Traction for Unstable Comminuted Intra–articular Fracture–Dislocations of the Proimal Interphalangeal Joint, The Journal of Hand Surgery Jul. 1995, Morgan et al.

*Primary Examiner*—Michael Buiz
*Assistant Examiner*—Vy Q. Bui
*Attorney, Agent, or Firm*—Calfee, Halter & Griswold LLP

[57] ABSTRACT

An external fixation apparatus for reduction and distraction of a joint injury such as fracture or dislocation of the proximal and distal bones of a joint from a location external to the soft tissue of a patient. The device including a proximal fixator, a distal fixator, a proximal wire inserted through the proximal fixator and into a proximal bone, a distal wire inserted through the distal fixator and into a distal bone, and an adjustable distraction mechanism connecting said proximal and distal fixators.

19 Claims, 4 Drawing Sheets

U.S. PATENT DOCUMENTS

| | | |
|---|---|---|
| 4,611,586 | 9/1986 | Agee et al. . |
| 4,620,533 | 11/1986 | Mears . |
| 4,621,627 | 11/1986 | DeBastiani et al. . |
| 4,628,919 | 12/1986 | Clyburn . |
| 4,628,921 | 12/1986 | Rousso . |
| 4,628,922 | 12/1986 | Dewar . |
| 4,662,365 | 5/1987 | Gotzen et al. . |
| 4,696,293 | 9/1987 | Ciullo . |
| 4,714,076 | 12/1987 | Comte et al. . |
| 4,724,827 | 2/1988 | Schenck . |
| 4,730,608 | 3/1988 | Schleiin . |
| 4,745,913 | 5/1988 | Castaman et al. . |
| 4,747,400 | 5/1988 | Koeneman et al. . |
| 4,757,809 | 7/1988 | Koeneman et al. . |
| 4,823,781 | 4/1989 | Buchanan . |
| 4,828,277 | 5/1989 | De Bastiani et al. . |
| 4,848,368 | 7/1989 | Kronner . |
| 4,869,242 | 9/1989 | Galluzzo . |
| 4,895,141 | 1/1990 | Koeneman et al. . |
| 4,922,896 | 5/1990 | Agee et al. . |
| 4,923,458 | 5/1990 | Fischer . |
| 4,941,481 | 7/1990 | Wagenknecht . |
| 4,942,872 | 7/1990 | Jawish . |
| 4,944,742 | 7/1990 | Clemow et al. . |
| 4,946,179 | 8/1990 | De Bastiani et al. . |
| 4,978,348 | 12/1990 | Ilizarov . |
| 4,988,349 | 1/1991 | Pennig . |
| 4,998,935 | 3/1991 | Pennig . |
| 5,019,077 | 5/1991 | De Bastiani et al. . |
| 5,021,054 | 6/1991 | Monfardini et al. . |
| 5,024,618 | 6/1991 | Tepic . |
| 5,026,372 | 6/1991 | Sturtzkopf et al. . |
| 5,026,374 | 6/1991 | Dezza et al. . |
| 5,047,029 | 9/1991 | Aebi et al. . |
| 5,074,865 | 12/1991 | Fahmy . |
| 5,098,432 | 3/1992 | Wagenknecht . |
| 5,100,403 | 3/1992 | Hotchkiss et al. . |
| 5,102,411 | 4/1992 | Hotchkiss et al. . |
| 5,108,394 | 4/1992 | Kurokawa et al. . |
| 5,112,331 | 5/1992 | Miletich . |
| 5,152,280 | 10/1992 | Danieli . |
| 5,160,335 | 11/1992 | Wagenknecht . |
| 5,167,661 | 12/1992 | Wagenknecht . |
| 5,192,281 | 3/1993 | de la Caffiniere . |
| 5,203,783 | 4/1993 | Harle . |
| 5,207,676 | 5/1993 | Canadell et al. . |
| 5,209,750 | 5/1993 | Stef . |
| 5,242,447 | 9/1993 | Borzone . |
| 5,275,599 | 1/1994 | Zbikowski et al. . |
| 5,292,322 | 3/1994 | Faccioli et al. . |
| 5,300,072 | 4/1994 | Aghion . |
| 5,304,177 | 4/1994 | Pennig . |
| 5,314,426 | 5/1994 | Pohl et al. . |
| 5,320,622 | 6/1994 | Faccioli et al. . |
| 5,320,623 | 6/1994 | Penning . |
| 5,330,474 | 7/1994 | Lin . |
| 5,330,476 | 7/1994 | Hiot et al. . |
| 5,334,202 | 8/1994 | Carter . |
| 5,342,360 | 8/1994 | Faccioli et al. . |

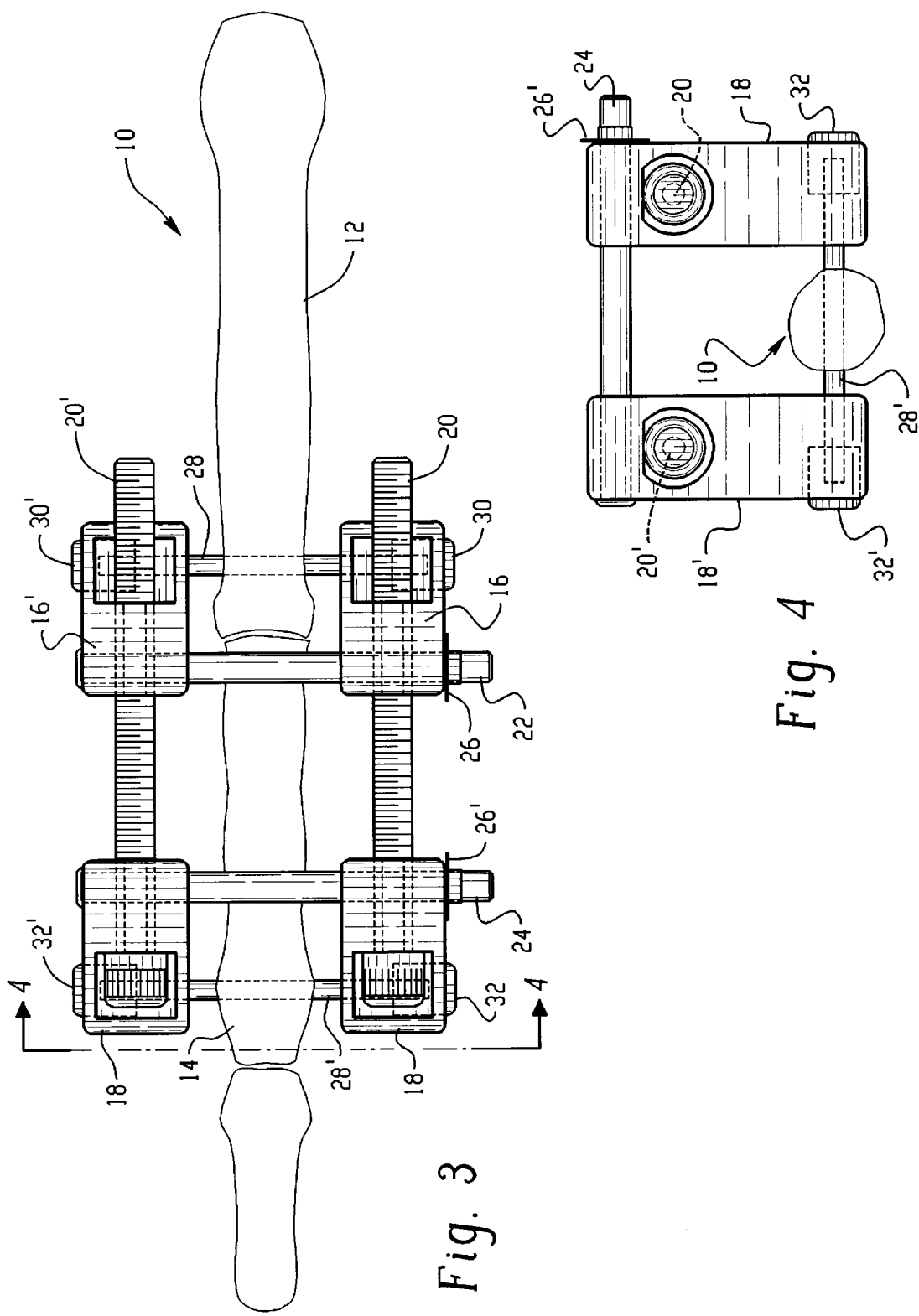

EXTERNAL DISTRACTOR/FIXATOR FOR THE MANAGEMENT OF FRACTURES AND DISLOCATIONS OF INTERPHALANGEAL JOINTS

This application claims the benefit of U.S. Provisional Application Ser. No. 60/002,913 filed Aug. 29, 1995, and is incorporated herein by reference.

BACKGROUND OF THE INVENTION

The present invention generally relates to an apparatus for externally fixing a joint fracture or dislocation. In particular, the present invention provides an apparatus that fixes a joint injury, such as a joint fracture or dislocation while allowing distraction coupled with dynamic movement and flexion of the fractured/dislocated joint.

It is well known in the art to place fractures, particularly comminuted fractures, under distraction to prevent compressive forces, such as those transmitted by tendons and ligaments, from collapsing the bone from its reduced and stabilized position during healing. For example, the proximal interphalangeal (PIP) joint of a finger is commonly injured resulting in a comminuted fracture or fracture/dislocation. Often, a comminuted joint injury such as those to the PIP joint can be adequately treated by traditional means. These traditional and well-known methods include fixation or splinting, but sometimes more traumatic injuries occur to the PIP joint that can be difficult to effectively manage by these traditional methods because these traditional methods do not alleviate post-trauma complications. Specifically, a noted effect of the healing process that leads to post-trauma complications is stiffness of joints and deterioration of cartilage tissue of the fractured bone or dislocated joint.

To treat these more traumatic PIP joint injuries, fixation can be combined with distraction and early motion of the joint. Early mobilization of the joint tends to produce better long term function. By coupling fixation with early distraction and mobilization of the fractured PIP joint, potential problems such as contracture, loss of motion, and post-traumatic arthritis to the finger may be avoided.

As stated above, in the past, other treatment methods have been used to treat these PIP joint fractures. Such treatment techniques include open reduction and internal fixation, volar plate arthoplasty, splinting, external fixation and distraction. Dynamic distraction has been used as treatment for comminuted fractures of the PIP joint to limit the aforementioned complications. Dynamic distraction combines the treatment method of distraction with early movement and mobilization of the joint to create a treatment method for these difficult PIP joint fractures.

In recent years, new methods to manage these difficult injuries have been developed. Schenck, in U.S. Pat. No. 4,724,827, discloses a dynamic distraction method. The Schenck device utilizes a cast to immobilize the wrist joint and any other additional joints of the hand and fingers, as needed. An actuator is connected to the cast. The actuator forms a vertical hoop about the distal tip of the broken finger with the proximal joint at the radial center of the hoop. The finger, at its distal ends, is then connected by elastic bands to the hoop to maintain distal distraction. The bands are slidable along the hoop so as to provide passive motion in an effort to minimize cartilage deterioration during the healing process A second device attempting to alleviate the complications associated with PIP joint fractures has been described by Hotchkiss. The Hotchkiss Compass Hinge, as the invention is known, uses a hinge with a worm gear to stabilize and distract fractures of the PIP joint. The Hotchkiss Compass Hinge is applied unilaterally to the fractured digit. The Compass Hinge has a proximal pin block and a distal pin block. First, an axis pin, usually formed from a Kirschner wire, is set through the PIP axis of rotation. Once the axis pin is in place, the device's hinge is slid over the pin, and the proximal and distal pin blocks are then affixed to the injured finger by pinning the blocks in place to the respective bones. The two portions of the device that comprise the hinge are then affixed to the blocks. A worm gear between and connecting the hinge portions limits the movement of the joint while also providing some distraction, but the device can only be applied unilaterally. Furthermore, due to the bulky and cumbersome nature of the device its application is realistically limited to border digits, specifically the index and small fingers.

Another well-known distraction device is the force couple wire type device described in 1987 by Agee. This device is hand crafted by a surgeon during an operation. The device is formed from three Kirschner wires ("K-wire") with two of the K-wires being smooth and the third wire being threaded. After reducing the fracture, the threaded K-wire is screwed into the dorsal portion of the joint so that it is vertical and perpendicular to the dorsal bone. The first smooth wire is inserted through the distal portion of the joint with the wire being parallel to the plane of the finger and parallel to the joint's axis of rotation. The second K-wire is then inserted proximally and parallel to the plane of the first K-wire. The distal K-wire is bent ninety degrees just outside the skin on both lateral sides of the finger. A notch is made above each bend in the distal wire, and an elastic band is placed to engage both notches and connect the distal wire to the threaded wire. The proximal K-wire is bent on each side and connected under the finger.

While devices applying distraction are known, these devices are often connected in a manner in which the distraction is difficult to maintain, the device itself may cause the digit to deviate, the device may be cumbersome and limited in its applicability to border digits and the devices are limited in their dynamic capabilities.

The present device provides improved reduction of the joint coupled with dynamic distraction.

SUMMARY OF THE INVENTION

The device of the present application includes an improved external fixation apparatus for stabilization, reduction and distal distraction of a bone joint fracture. The apparatus further allows for dynamic movement of the bone joint between a flexed position and an extended position while fixation, stabilization and distraction is ongoing.

The device includes a proximal fixator and a distal fixator. Wires or pins are inserted into a fixator, passed through the bone and received by the opposed fixator. This fixation is done both proximally and distally at the fractured joint. Each proximal and distal fixator placed on the same side of the digit are connected by an adjustable tension means so as to place the fractured joint under distraction. As the fracture heals, the tension means can be adjusted to vary distraction on the joint. Also, the design of the apparatus inherently allows the fractured joint to be moved without affection while being distracted. Thus, the continuous distraction prevents collapse of the fractured bone during healing, while dynamic motion, via flexion of the fractured joint, minimizes cartilage deterioration, digit deviation and contracture during the healing and restoration process.

These and other advantages of the invention will be described in greater detail below with reference to the accompanying drawings.

BRIEF DESCRIPTION OF THE DRAWINGS

FIG. 3 illustrates a schematic top view of the device shown in FIG. 2;

FIG. 4 illustrates a schematic end view of the present invention taken along the line 4—4 of FIG. 3;

DETAILED DESCRIPTION OF THE INVENTION

The invention includes an apparatus for external fixation of injured bone joints and placing the injured bone joints under continuous and adjustable distraction while still allowing movement of the joint. Frequently, complex fracture/dislocations of joints occur. In particular, one such area where these complex fracture/dislocations occur is the proximal interphalangeal joint (PIP) of the finger.

External fixation can be used to stabilize and reduce such PIP joint fractures/dislocations. Furthermore, placing such a fractured/dislocated PIP joint under gradual distraction can eliminate the side-effects of these complex fractures which include condistraction, loss of motion and deviation of the finger. The present invention reduces and stabilizes a fractured/dislocated joint, places the joint under distraction and also allows for dynamic movement of the joint while being stabilized and distracted. Also, ease of application, facile positioning of the device, flexibility in frame design and the ability to apply the device to any digit, regardless of its location, is desirable and needed.

Figure 1:
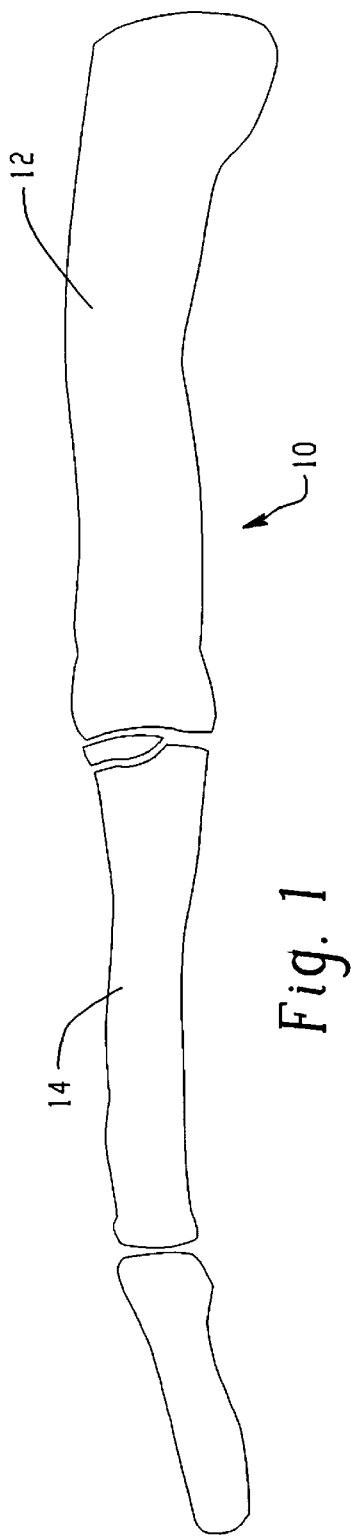
FIG. 1 is a side view of a finger having a fracture/dislocation of a proximal interphalangeal joint.

FIG. 1 represents a finger, generally shown at 10, having a fracture/dislocation of the proximal interphalangeal joint. The proximal bone of the joint is seen at 12, while the distal bone is seen at 14. As shown in FIG. 1, a proximal interphalangeal joint fracture can be a difficult injury to treat. Long-term morbidity ranges from stiffness and motion loss to significant joint incongruity necessitating later fusion of the joint.

Figure 2:
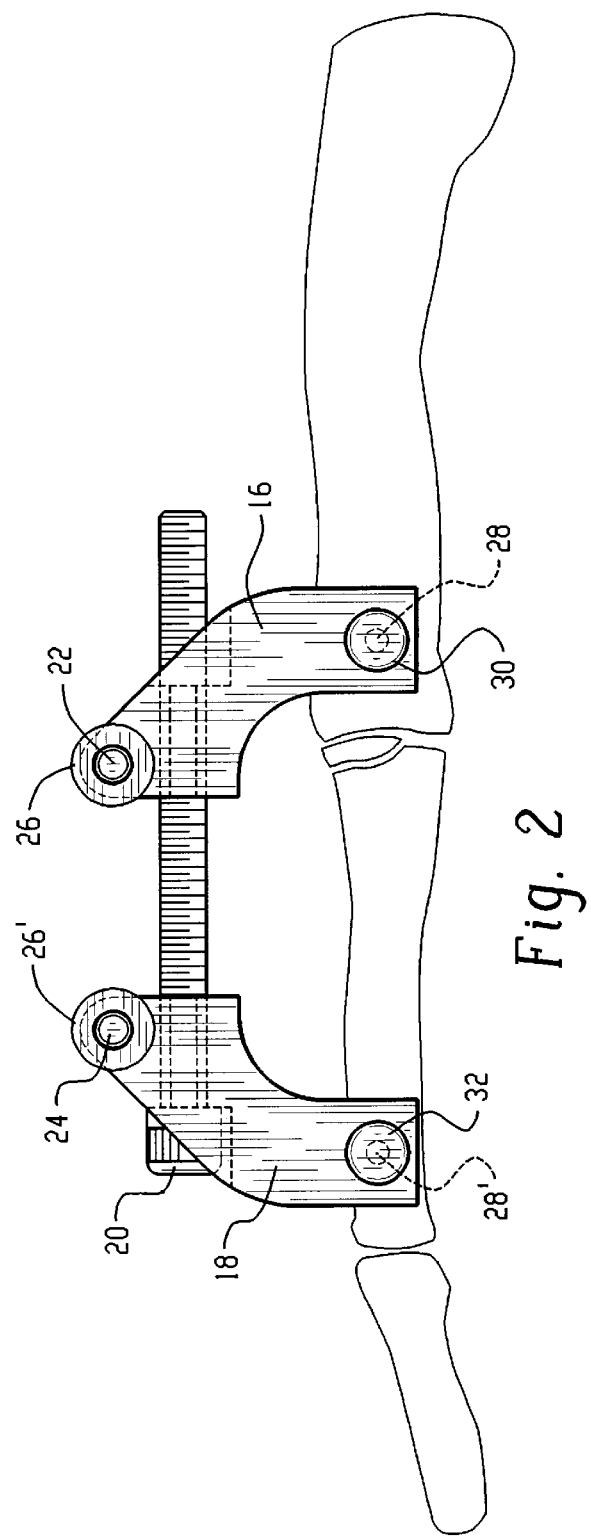
FIG. 2 illustrates a schematic side view of the present invention for an external fixation device for bilateral reduction and distraction of a joint injury.

One preferred embodiment of the device of the present application is shown in FIG. 2. As seen in FIG. 2, this embodiment is preferably for external bilateral reduction and distraction of a PIP joint fracture. The apparatus includes a pair of proximal fixators 16, 16' and a pair of distal fixators 18, 18', also shown in FIG. 3. Each respective pair of fixators is positioned external to the digit and opposite each other.

As further shown in FIG. 2, an adjustable distraction rod 20 is inserted through and connects the proximal and distal fixators located ipsilaterally of the digit. The distraction rod places the joint under distraction to stabilize the joint. This distraction rod should be adjustable so that distraction can be varied, as needed, during the healing process. Preferably, the distract rod is a threaded rod that can be adjusted by an Allen wrench or other such implement.

Proximal and distal guide rods 22, 24 are also provided, as shown in FIG. 2. The proximal guide rod 22 externally and contralaterally connects the proximal fixators 16, 16', and the distal guide rod 24 externally and contralaterally connects the distal fixators 18, 18'. A push nut 26, 26' or other such locking device is applied to each guide rod to hold it in place so as to maintain an appropriate distance between the fixators. By assembling the fixators contralaterally with their respective guide rod and ipsilaterally with their respective adjustable distraction rod, a template is formed to aid in application, placement and position of the device. Collectively, the fixators, guide rods and distraction rods are herein referred to as the "sub-assembly." Once the sub-assembly is constructed, it can be placed over and around the injured digit 10. Since the fixators are preferably radiolucent, the proper position of the device can be determined by fluoroscope before fixation to the finger. Also, guide wires 28, 28' can be viewed under fluoroscope during insertion through the fixators and bone of the finger to ensure proper position and deployment.

As shown in FIGS. 3 and 4, if the fixators are properly positioned, a proximal wire 28, is inserted through a proximal fixator 16, through the corresponding bone and finally through the opposing proximal fixator 16'. Preferably, the wire is of the smooth Kirschner type with a diameter of approximately 1.1 mm. Once the wires are in place, end caps or plugs 30, 30' are affixed to the respective ends of each wire. This procedure is then repeated for the distal portion with wire 28 inserted therethrough and corresponding end-caps 32, 32'.

Figure 8A:
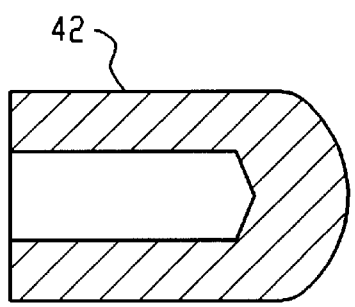
FIG. 8A illustrates a side view, in cross-section, of straight end caps for use in dynamic fixation.
Figure 8B:
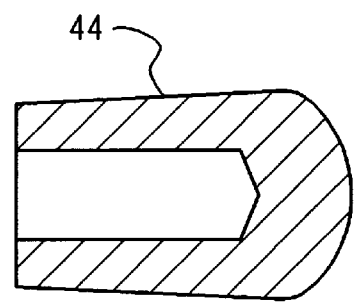
FIG. 8B illustrates a side view, in cross-section, of tapered end caps for use with static fixation.

Once this device is applied, the adjustable distraction rods 20, 20' may be utilized to place the fractured joint 10 under variable bilateral tension while still allowing flexion at the joint. Thus, the bilateral fixation device limits the deviation and contracture associated with these fractures by allowing movement while under distraction and has ease of application. As shown in FIGS. 8A and 8B, end caps (see referenced elements 30, 30' and 32, 32' of FIGS. 3 and 4) can either be of the dynamic type (see straight end caps 42 of FIG. 8A) for use with dynamic fixation, or of the static type (see tapered end caps 44 of FIG. 8B) for use with static fixation. If static fixation is desired, the tapered end caps are pressed in place, constricting onto and holding the K-wire fixed. This prevents any relative motion between the fixator and wire. If dynamic fixation is desired, the straight end caps are pressed into place over the cut K-wire ends. This allows motion while maintaining the distraction/compression.

Figure 5:
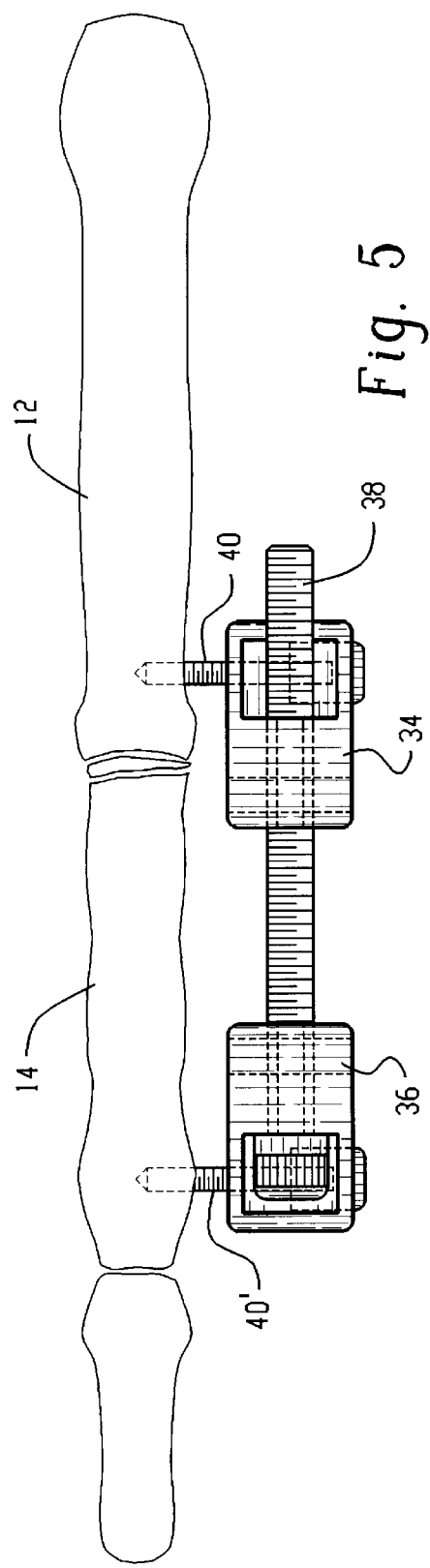
FIG. 5 illustrates an alternate embodiment of the present invention showing a schematic top view a fixation device for unilateral deployment.
Figure 6:
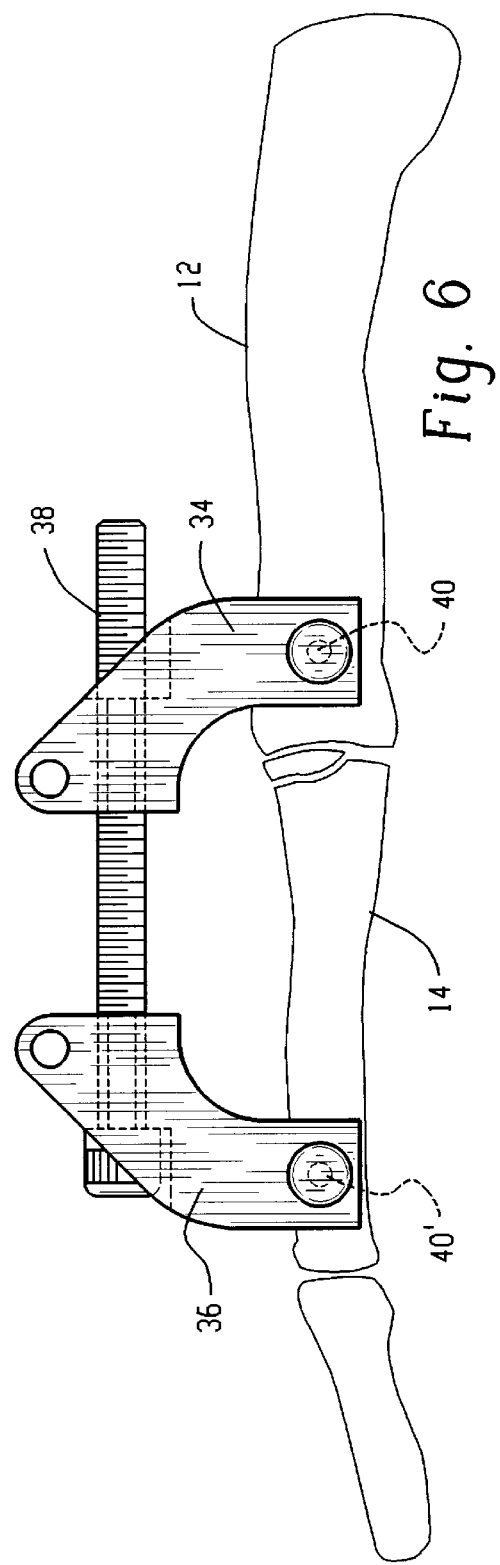
FIG. 6 illustrates a schematic side view of the device of FIG. 5.
Figure 7:
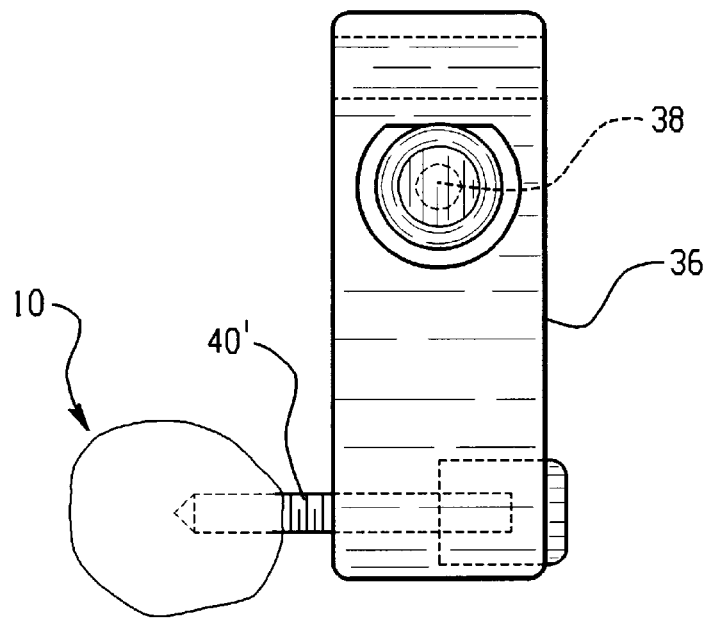
FIG. 7 illustrates a schematic end view of the device of FIG. 6.

As shown in FIGS. 5–7, another alternate embodiment of the invention contemplates unilateral deployment. In this embodiment, a proximal fixator 34 and a distal fixator 36 are connected by an adjustable distraction rod 38. After positioning this sub-assembly and checking the position via fluoroscope or other imaging means, fixation wires 40, 40' are inserted through the respective fixators 34, 36' and into the bones 12, 14. In this unilateral embodiment, the fixation wires 40, 40' are preferably of a threaded Kirschner type and should be preferably inserted approximately halfway into the bone. Once the device is attached to the bone joint 10 and the fracture reduced and stabilized, the adjustable distraction rod 38 may be manipulated to place the fracture under proper distraction while still allowing for movement of the joint. As shown in FIGS. 8A and 8B, end caps (see referenced elements 30, 30' and 32, 32' of FIGS. 3 and 4) can either be of the dynamic type (see straight end caps 42 of FIG. 8A) for use with dynamic fixation, or of the static type (see tapered end caps 44 of FIG. 8B) for use with static fixation. If static fixation is desired, the tapered end caps are pressed in place, constricting onto and holding the K-wire fixed. This prevents any relative motion between the fixator and wire. If dynamic fixation is desired, the straight end caps are pressed into place over the cut K-wire ends. This allows motion while maintaining the distraction/compression.

While this invention has been disclosed with reference to specific embodiments, it is apparent that other embodiments and equivalent variations of this invention may be devised without departing from the spirit of the invention and the scope of the claims.

I claim:

1. An external fixation apparatus for the dynamic distraction of a bone joint injury from a location external to the soft tissue of a patient, said joint having a proximal bone and a distal bone, comprising:

opposing proximal fixators and opposing distal fixators;

a proximal wire for insertion through the proximal bone, the proximal wire being mounted to the proximal fixators in a manner allowing relative movement between the proximal wire and the proximal fixators for dynamic fixation of said joint;

a distal wire for insertion through the distal bone, the distal wire being mounted to the distal fixators; and at least one adjustable distraction rod connecting said proximal and distal fixators.

2. The external fixation apparatus of claim 1, wherein said wires are Kirschner type smooth wires.

3. The external fixation apparatus of claim 1, further comprising guide rods to connect said opposing fixators.

4. The external fixation apparatus of claim 1, further comprising a locking mechanism capable of fixing said guide rods in place.

5. The external fixation apparatus of claim 1, wherein said adjustable distraction rods are threaded.

6. An external fixation apparatus for dynamic distraction of a joint injury from a location external to the soft tissue of a patient, said joint having a proximal bone and a distal bone, comprising:

a proximal and a distal fixator;

at least one proximal wire insertable into a proximal bone and mounted to said proximal fixator in a manner allowing relative movement between the proximal wire and the proximal fixator for dynamic fixation of said joint;

at least one distal wire insertable into the distal bone and mounted to said distal fixator; and an adjustable distraction mechanism connecting said proximal and distal fixators.

7. The external fixation apparatus of claim 6, wherein said at least one wire is a Kirschner type threaded wire.

8. The external fixation apparatus of claim 1 further comprising proximal wire end caps rotatable mounting the proximal wire in the proximal fixators.

9. The external fixation apparatus of claim 8 further comprising distal wire end caps.

10. The external fixation apparatus of claim 1 wherein said adjustable distraction rod is lockable.

11. The external fixation apparatus of claim 1 wherein said proximal and distal fixators are radiolucent.

12. The external fixation apparatus of claim 1 wherein the proximal wire comprises a single proximal wire.

13. The external fixation apparatus of claim 6 wherein said proximal and distal fixators are radiolucent.

14. Apparatus for the treatment of bone joint injuries, the joint having a proximal bone and a distal bone, the apparatus comprising:

(a) a frame for positioning external to the soft tissue of a patient, the frame including a pair of proximal fixators for positioning on opposite sides of the proximal bone, a pair of distal fixators for positioning on opposite sides of the distal bone, and at least one adjustment rod for connecting the proximal and distal fixators for achieving selective reduction and distraction of the joint;

(b) a proximal wire for inserting through the proximal bone and mounting in the proximal fixators; and (c) at least one distal wire for inserting through the distal bone and mounting in the distal fixators;

wherein the proximal wire is adapted for mounting in the proximal fixators in a manner allowing relative motion between the proximal wire and the proximal fixators thereby allowing the proximal and distal bones to move with respect to one another at said joint while the apparatus maintains the joint stabilized and distracted.

15. Apparatus for the treatment of bone joint injuries, the joint having a proximal bone and a distal bone, the apparatus comprising:

(a) a frame for positioning external to the soft tissue of a patient, the frame including a pair of proximal fixators for positioning on opposite sides of the proximal bone, a pair of distal fixators for positioning on opposite sides of the distal bone, and at least one adjustment rod for connecting the proximal and distal fixators for achieving selective reduction and distraction of the joint;

(b) a single proximal wire for inserting through the proximal bone and mounting in the proximal fixators; and (c) at least one distal wire for inserting through the distal bone and mounting in the distal fixators;

wherein the proximal wire is adapted for mounting in the proximal fixators in a manner allowing relative motion between the proximal wire and the proximal fixators thereby allowing the proximal and distal bones to move with respect to one another at said joint while the apparatus maintains the joint stabilized and distracted.

16. Apparatus for the treatment of bone joint injuries, the joint having a proximal bone and a distal bone, the apparatus comprising:

(a) a frame for positioning external to the soft tissue of a patient, the frame including a proximal fixator, a distal fixator, and an adjustment rod for connecting the proximal and distal fixators for achieving selective reduction and distraction of the joint;

(b) a proximal wire for inserting through the proximal bone; and (c) at least one distal wire for inserting through the distal bone and mounting in the distal fixators;

wherein the proximal wire is adapted for mounting in the proximal fixator in a manner allowing relative motion between the proximal wire and the proximal fixator thereby allowing the proximal and distal bones to move with respect to one another at said joint while the apparatus maintains the joint stabilized and distracted.

17. The apparatus of claim 16, wherein the apparatus is adapted to be used in a dynamic mode in which the proximal and distal bones are able to move with respect to one another at said joint while the apparatus maintains the joint stabilized and distracted, and further wherein the apparatus is adapted to be used in a static mode in which the proximal and distal bones are not able to move with respect to one another at said joint while the apparatus maintains the joint stabilized and distracted, the proximal wire being mounted for relative movement with respect to the proximal fixator when the apparatus is in the dynamic mode.

18. Apparatus for the dynamic fixation of a joint injury from a location external to the soft tissue of a patient, the apparatus allowing selective reduction and distraction of the joint injury, the apparatus comprising:

a pair of proximal fixators;

a pair of distal fixators;

a proximal wire insertable through a proximal bone of said joint, the proximal wire being mounted to the proximal fixators in a manner allowing relative movement between the proximal wire and the proximal fixators thereby allowing the proximal fixators to rotate relative to the proximal bone;

at least one distal wire insertable through a distal bone of said joint, the distal wire being mounted to said distal fixators; and an adjustable distraction mechanism connecting said proximal and distal fixators.

19. An apparatus for the dynamic fixation of a joint injury from a location external to the soft tissue of a patient, the apparatus allowing selective reduction and distraction of the joint injury, the apparatus comprising:

a proximal fixator;

a distal fixator;

a proximal wire insertable through a proximal bone of said joint, the proximal wire being mounted to the proximal fixator in a manner allowing relative movement between the proximal wire and the proximal fixator thereby allowing the proximal fixator to rotate relative to the proximal bone;

at least one distal wire insertable through a distal bone of said joint, the distal wire being mounted to said distal fixator; and an adjustable distraction mechanism connecting said proximal and distal fixators.

* * * * *